US00PP21322P2

(12) United States Plant Patent
Smith

(10) Patent No.: US PP21,322 P2
(45) Date of Patent: Sep. 28, 2010

(54) ***CHRYSANTHEMUM* PLANT NAMED 'BRUNETTE YOBARBIE'**

(50) Latin Name: *Chrysanthemum×morifolium*
Varietal Denomination: Brunette Yobarbie

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,754

(22) Filed: Jul. 7, 2009

(51) Int. Cl.
*A01H 5/00* (2006.01)

(52) U.S. Cl. ..... Plt./290

(58) Field of Classification Search ..... Plt./290
See application file for complete search history.

*Primary Examiner*—June Hwu
(74) *Attorney, Agent, or Firm*—S. Matthew Edwards

(57) ABSTRACT

A new *Chrysanthemum* plant named 'Brunette Yobarbie,' particularly distinguished by the medium size decorative-type, orange-bronzed flowers, medium green foliage, freely branching, medium size upright and mounded habit.

1 Drawing Sheet

Latin name of the genus and species of the plant claimed: *Chrysanthemum×morifolium.*

Varietal denomination: 'Brunette Yobarbie'.

BACKGROUND OF THE NEW PLANT

The present invention comprises a new *Chrysanthemum,* botanically known as *Chrysanthemum×morifolium,* and hereinafter referred to by the variety name 'Brunette Yobarbie.'

The new cultivar 'Brunette Yobarbie' has medium size decorative-type, orange-bronzed flowers, medium green foliage, freely branching, medium size upright and mounded habit.

'Brunette Yobarbie' originates as a natural whole plant mutation of 'Yobarbie,' U.S. Plant Pat. No. 17,008. 'Brunette Yobarbie' was discovered and selected by the inventor as a single flowering plant within a population of the parent cultivar in a field trial in Alva, Florida in December 2005. The parent cultivar 'Yobarbie' has lavender flower color, shorter plant habit, smaller foliage size, and a little faster flowering response than 'Brunette Yobarbie.'

The first act of asexual reproduction of 'Brunette Yobarbie' was accomplished when vegetative cuttings were propagated from the initial selection in February 2006 in a controlled environment in Alva, Fla.

BRIEF SUMMARY OF INVENTION

Horticultural examination of plants grown from cuttings of the plant initiated in February 2006, and continuing thereafter, has demonstrated that the combination of characteristics as herein disclosed for 'Brunette Yobarbie' are firmly fixed and are retained through successive generations of asexual reproduction.

'Brunette Yobarbie' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

Plant Breeder's Rights for this cultivar have not been applied for. 'Brunette Yobarbie' has not been made publicly available more than one year prior to the filing of this application.

BRIEF DESCRIPTION OF THE PHOTOGRAPHS

Figure 1:
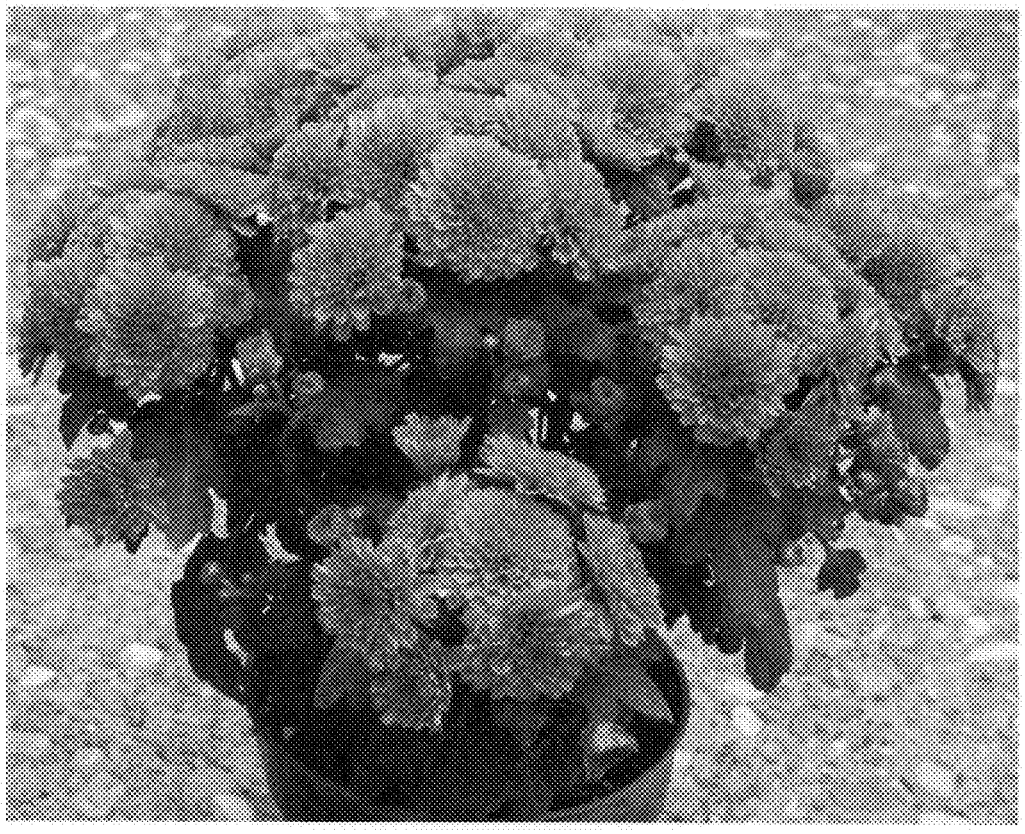
Figure 2:
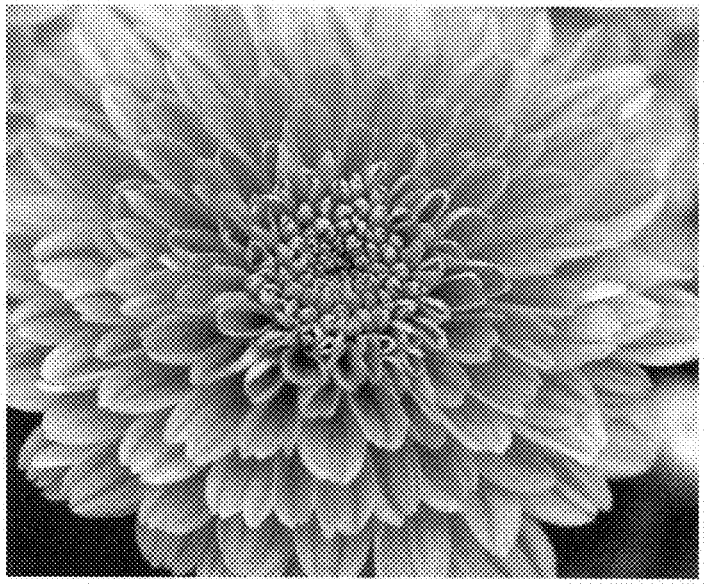

The accompanying photographic drawing shows typical flower and foliage characteristics of 'Brunette Yobarbie' with colors being as true as possible with an illustration of this type. The photographic drawing shows in FIG. 1 a flowering potted plant of the new variety, and in FIG. 2 a close-up of the flowers.

DETAILED BOTANICAL DESCRIPTION

The plant descriptions and measurements were taken in mid-May 2009. The aforementioned photographs were taken in early June 2009 in Salinas, Calif.

These plants were started and grown in Alva, Fla. and were shipped to California in May 2009. Plants were grown under conditions which approximate those generally used in commercial potted *Chrysanthemum* production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'BRUETTE YOBARBIE' AND A SIMILAR VARIETY

| | 'Brunette Yobarbie' | 'Yoandrea' (U.S. Plant Pat. No. 12,983) |
|---|---|---|
| Flower color: | Orange-bronzed | Yellow/red |
| Average quantity of disc florets: | 3-4 | About 10-15 |
| Foliage color: | Lighter | Darker |
| Peduncle length: | Shorter | Taller |
| Plant height: | Taller | Shorter |

Plant:
*Form, growth and habit.*—Herbaceous decorative garden-type; stems upright and outwardly spreading, freely branching, strong and moderately vigorous growth habit.
*Plant height.*—20-22 cm.
*Plant height (inflorescence included).*—24-25 cm.
*Plant width.*—33-36 cm.
*Garden performance and tolerance to weather.*—Good.
*Crop time to flowering.*—About 45-54 days.

Roots:
*Number of days to initiate roots.*—4 days at about 21 degrees C.
*Number of days to produce a rooted cutting.*—4 days at 21 degrees C.
*Type.*—Fine, fibrous, free branching.
*Color.*—RHS N155B but whiter.

Foliage:
*Arrangement.*—Alternate.
*Immature, leaf color, upper surface.*—RHS 137B with slight blotching of RHS 137A.
*Lower surface.*—Closest to RHS 137C.
*Mature, leaf color, upper surface.*—RHS 137B with more blotching of RHS 137A.
*Lower surface.*—RHS 137C.
*Length.*—5.4-5.9 cm.
*Width.*—4.3-4.6 cm.
*Shape.*—Ovate.
*Base shape.*—Attenuate.
*Apex shape.*—Mucronulate.
*Margin.*—Palmately lobed; slightly incised, serrate.
*Texture, upper surface.*—Bifid T-shaped hairs.
*Lower surface.*—Bifid T-shaped hairs.
*Color of veins, upper surface.*—RHS 147C.
*Color of veins, lower surface.*—RHS 147C.
*Petiole color.*—RHS 147C.
*Length.*—1.8-2.0 cm.
*Diameter.*—0.2 cm.
*Texture.*—Bifid T-shaped hairs.

Stem:
*Average quantity of main branches per plant.*—6-8.
*Average quantity of leaves per branch.*—10-12.
*Color of stem.*—RHS 146B.
*Length of stem.*—16-19 cm.
*Diameter.*—0.4-0.45 cm.
*Length of internodes.*—1.0-1.5 cm.
*Texture.*—Bifid T-shaped hairs.
*Color of peduncle.*—RHS 146B.
*Length of peduncle.*—2.3-2.5 cm.
*Peduncle diameter.*—0.2 cm.
*Texture.*—Heavily covered with Bifid T-shaped hairs.

Inflorescence:
*Type.*—Compositate type, solitary inflorescences (decorative-type) borne terminally above foliage, ray florets arranged acropetally on a capitulum.
*Blooming habit.*—Natural season flowering in about mid October.
*Average quantity of inflorescences per plant.*—About 110.
*Average quantity of inflorescences per lateral stem.*—About 15.
*Lastingness of individual blooms on the plant.*—About 4 weeks.
*Fragrance.*—Slightly spicy.

Bud (just before opening/showing color):
*Color.*—RHS 184A.
*Length.*—0.7-0.9 cm.
*Width.*—0.8-0.9 cm.
*Shape.*—Oblate.

Immature inflorescence:
*Diameter.*—2.7-3.0 cm.
*Color of ray florets, upper surface.*—Closest to RHS 172B.
*Lower surface.*—RHS 159B.

Mature inflorescence:
*Diameter.*—4.2-4.4 cm.
*Depth.*—1.2-1.4 cm.
*Total diameter of 'disc'.*—No disc showing.
*Receptacle height.*—0.3-0.5 cm.
*Receptacle diameter.*—0.5 cm.

Ray florets:
*Average quantity of florets.*—210 in numerous whorls.
*Color of florets, upper surface.*—RHS 172C overlaid with RHS 172B more heavily at apex with RHS 162B basally.
*Lower surface.*—Closest to RHS 159C.
*Length.*—1.7-1.8 cm.
*Width.*—0.6-0.7 cm.
*Shape.*—Elliptical to oblanceolate.
*Apex shape.*—Praemorse.
*Margin.*—Entire.
*Texture, upper surface.*—Papillose.
*Lower surface.*—Papillose.

Disc florets:
*Average quantity of florets.*—3-4.
*Color of florets.*—RHS 1B basally and RHS 12A towards the apex.
*Length.*—0.6-0.8 cm.
*Width.*—0.1 cm.
*Shape.*—Tubular, enlongated.
*Apex shape.*—Acute, 5 pointed.

Phyllaries:
*Average quantity.*—16-18.
*Color, upper surface.*—RHS 147B but a little more yellow-green.
*Lower surface.*—RHS 147B but a little more yellow-green.
*Length.*—0.6-0.8 cm.
*Width.*—0.2-0.35 cm.
*Shape.*—Mostly lanceolate, some more ligulate.
*Apex shape.*—Fused.
*Margins.*—Entire; papery and translucent.
*Texture, upper surface.*—Smooth and shiny.
*Lower surface.*—Bifid T-shaped hairs.

Reproductive organs:
*Gyneocium.*—Found on both floret types.
*Pisil quantity.*—1.
*Length.*—0.4-0.5 cm.
*Style color.*—RHS 1B.
*Style length.*—0.3 cm.
*Stigma color.*—RHS 7A.
*Stigma shape.*—Biparted.
*Ovary color.*—RHS 155C.
*Andreocium.*—Found on only disc florets.
*Stamens quantity.*—4-5.
*Color of filaments.*—RHS 1C.
*Length filaments.*—0.2-0.3 cm.
*Anther color.*—RHS 2C.
*Anther length.*—0.15-0.2 cm.

*Anther shape.*—Ligulate.

*Color of pollen.*—Not observed.

*Pollen amount.*—None observed.

*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Brunette Yobarbie,' substantially as illustrated and described herein.

* * * * *